United States Patent [19]
Anelli et al.

[11] Patent Number: 5,728,877
[45] Date of Patent: Mar. 17, 1998

[54] PROCESS FOR THE MANUFACTURING OF IODINATED CONTRAST AGENTS

[75] Inventors: Pier Lucio Anelli; Marino Brocchetta; Ornella Gazzotti; Fulvio Uggeri, all of Milan, Italy

[73] Assignee: Dibra S.p.A., Italy

[21] Appl. No.: 685,034

[22] Filed: Jul. 23, 1996

[30] Foreign Application Priority Data

Jul. 25, 1995 [IT] Italy .................. MI95A1612

[51] Int. Cl.$^6$ ............................ C07C 233/65
[52] U.S. Cl. ........................ 564/153; 424/9.254
[58] Field of Search ............ 564/153; 424/9.254

[56] References Cited

FOREIGN PATENT DOCUMENTS 0 185 130  6/1986  European Pat. Off. .

*Primary Examiner*—Shailendra Kumar
*Attorney, Agent, or Firm*—Nixon & Vanderhye

[57] ABSTRACT

A process for the preparation of compounds of general formula (I)

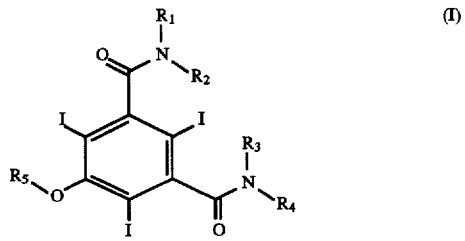

characterized in that the corresponding derivatives of general formula (II)

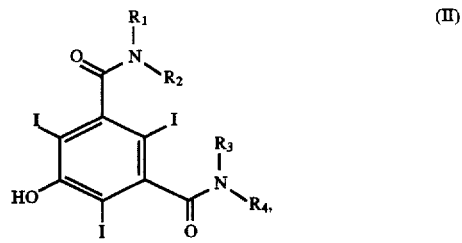

are reacted with the compounds of general formula (III)

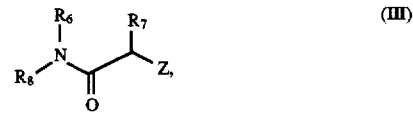

wherein

Z is halogen atom or a reactive residue of a sulfonic acid or a $-N^+(R_9)_3$ cation wherein $R_9$ is a ($C_1$–$C_6$) alkyl group and $R_1$, $R_2$, $R_3$, $R_4$, $R_5$ $R_6$ $R_7$ and $R_8$ are as herein defined.

5 Claims, No Drawings

PROCESS FOR THE MANUFACTURING OF IODINATED CONTRAST AGENTS

This invention refers to a new synthetic process especially for the manufacturing of derivatives of diamides of 5-alkoxy-2,4,6-triiodo-1,3-benzenedicarboxylic acids of general formula (I)

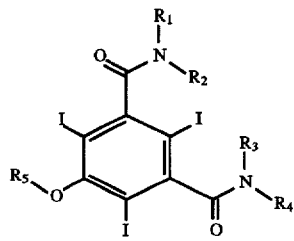

(I)

wherein $R_1$, $R_2$, $R_3$, $R_4$, which can be the same or different are, independently, H or a linear or branched $(C_1-C_{10})$ alkyl group, optionally substituted by 1–6 hydroxy and/or alkoxy groups, or a polyoxyalkyl group comprising from 1 to 10 oxygen atoms and from 3 to 30 carbon atoms, or $R_1$ and $R_2$ or $R_3$ and $R_4$, taken together, form a $(C_2-C_8)$ chain optionally interrupted by one or more N, O, S atoms;

$R_5$ is the group

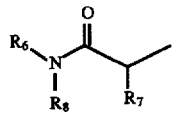

$R_6$ and $R_8$, which can be the same or different are, independently, H or a $(C_1-C_6)$ alkyl, hydroxyalkyl, alkoxyalkyl or alkoxyhydroxyalkyl group, $R_7$ is H or a $(C_1-C_3)$ alkyl, hydroxyalkyl or alkoxyalkyl group, characterized in that the corresponding derivatives of general formula (II)

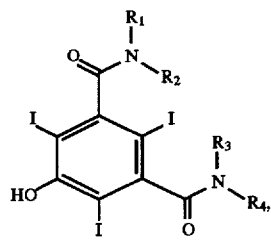

(II)

wherein $R_1$, $R_2$, $R_3$ and $R_4$ are as previously described and the hydroxy group on the benzene ring can be also present as salt of an alkali metal or alkaline-earth metal or a $(C_2-C_6)$ trialkylamine, are reacted with the compounds of general formula (III)

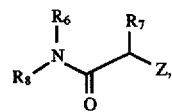

(III)

Z is halogen atom or a reactive residue of a sulfonic acid or a cation $-N^+(R_9)_3$ wherein $R_9$ is a $(C_1-C_6)$ alkyl group and $R_6$ $R_7$ and $R_8$ are as previously described.

The preparation of the compounds of general formula (I) has been previously described in patent EP 185130, which describes the synthesis of the above compounds starting from phenol precursors or from their salts according to Scheme 1.

SCHEME 1

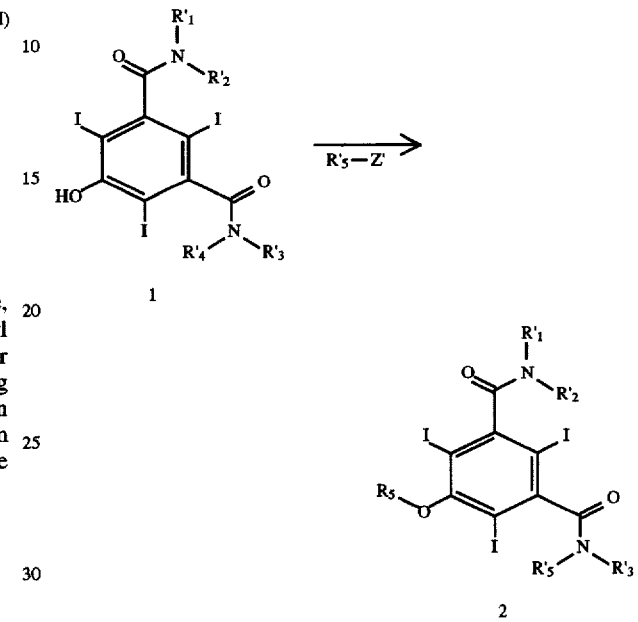

The above patent foresees the reaction of the phenol groups in the free form or the reaction in the salified form with alkali or alkaline-earth metals with a reactive compound $R_5'$—$Z'$, preferably containing an alkoxycarbonylalkyl group and a reactive group $Z'$, with the same meaning for Z in this invention and the successive transformation of the ester group into amido group, by reaction with ammonia or with differently substituted amines.

The resulting products of formula 2 can be useful also as intermediates as described in patent EP 365541, for the preparation of X-ray contrast media by Smiles rearrangement.

Differently from patent EP 185130, the process of this invention, foresees only one step for the production of the desired product, i.e. the direct reaction of phenol precursors with a reactive compound already containing the desired amido group, as from Scheme 2.

SCHEME 2

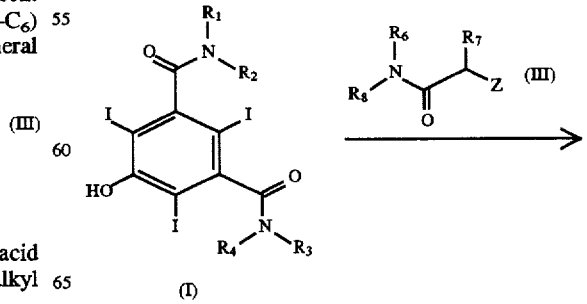

-continued
SCHEME 2

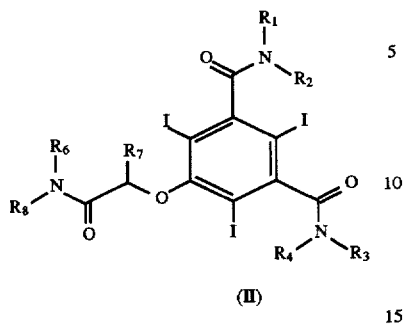

The use of an amido derivative in the reaction of nucleophilic substitution to give derivatives of general formula (I) instead of an ester derivative, as described in patent EP 185130, leads to a considerable decrease in the number of synthetic steps required to obtain the final compounds of general formula (II).

The application of the process of this invention is particularly interesting for the preparation of an intermediate in the synthesis of S—N,N'-bis[2-hydroxy-1-(hydroxymethyl) ethyl]-5-[(2-hydroxy-1-oxopropyl)amino]-2,4,6triiodo-1,3-benzenedicarboxamide, commonly known as IOPAMIDOL, which is one of the world best-seller in the field of non-ionic X-ray contrast media.

The synthesis method described in EP 365541, foresees the formation of intermediate 3, according to the procedure described in the already cited EP 185130, followed by Smiles rearrangement, as shown in Scheme 3.

-continued
SCHEME 3

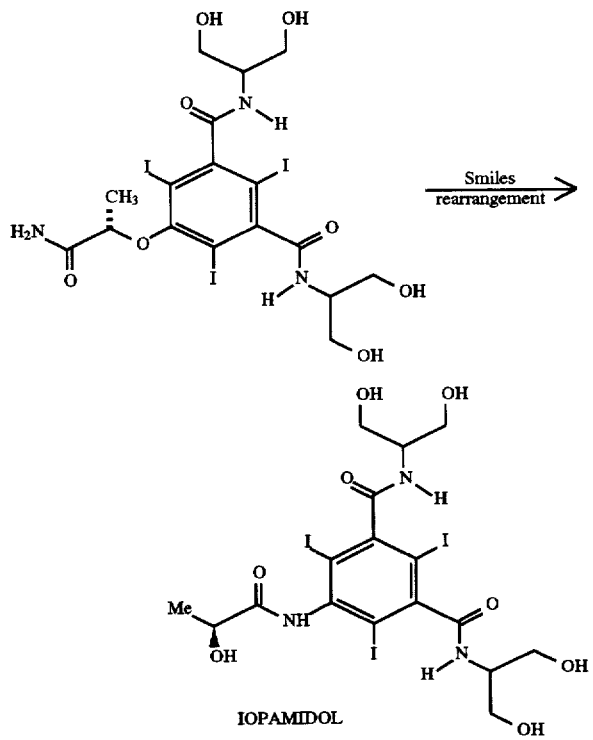

A more straightforward preparation for iopamidol can be carried out by the sequence of reactions shown in Scheme 4 and described in Examples 1, 2 and 4.

SCHEME 3

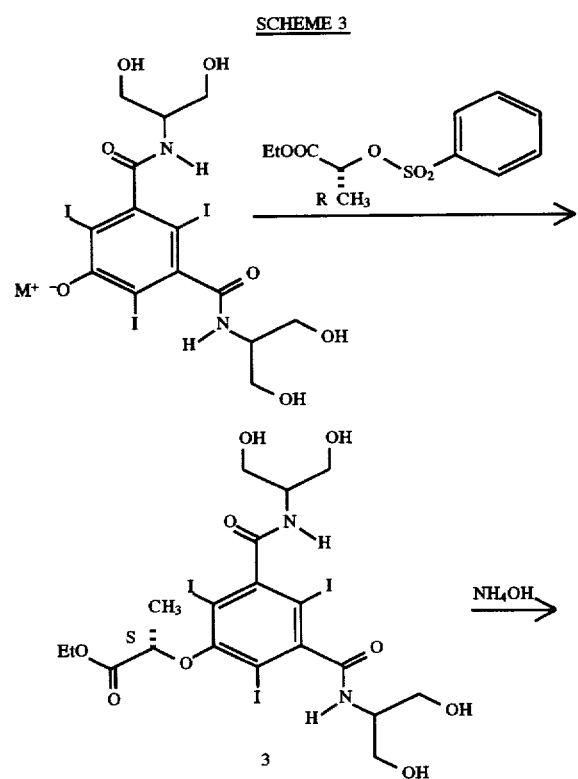

SCHEME 4

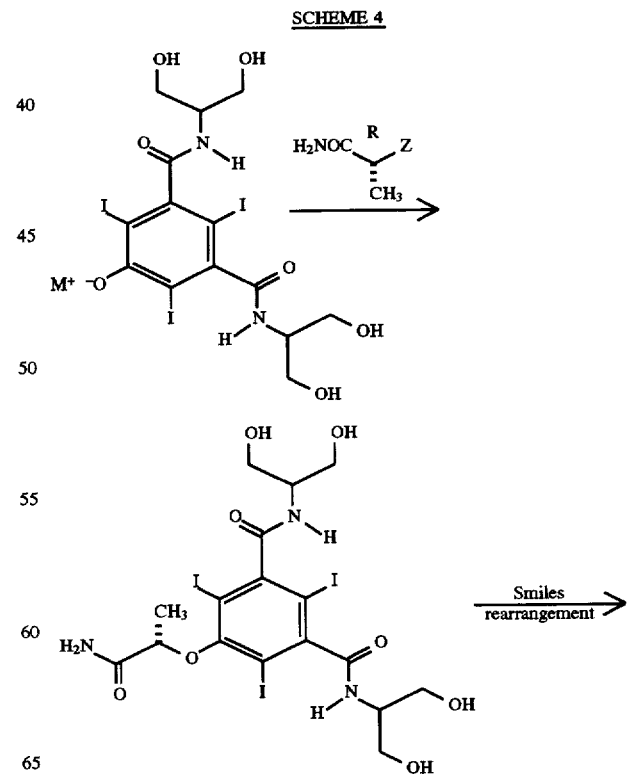

-continued
SCHEME 4

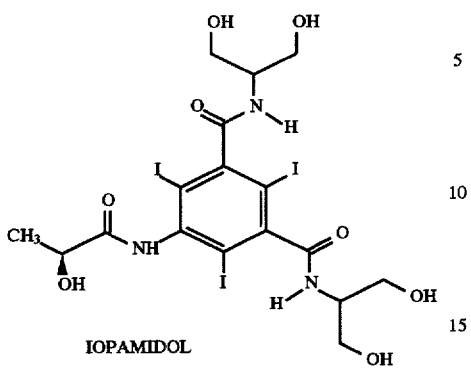

IOPAMIDOL

More generally, in order to carry out the process of this invention, the salts of phenol derivatives of general formula (II) are particularly suitable for the reaction of etherification, in particular their sodium, potassium and calcium salts.

The reactive group Z in compounds of general formula (III) is as definition a halide Cl, Br and I, or a reactive residue of a sulfonic acid (for instance methanesulfonyloxy ($MeSO_2O^-$), benzenesulfonyloxy ($PhSO_2O^-$), nitrobenzenesulfonyloxy ($p\text{---}NO_2PhSO_2O^-$), toluensulfonyloxy ($TsO^-$), and so on), preferably toluenesulfonyloxy, or a $N^+(R_9)_3$ cation wherein $R_9$ is as previously defined.

Particularly preferred are the following reaction conditions for the process of this invention:

the sodium salt of the phenol compound of formula (II);

the stoichiometric ratio compound of formula (III)/ compound of formula (II) is equal to 2;

the formation of a ether bond between the compounds of general formula (II) and the compounds of general formula (III) is carried out at a temperature comprised between room temperature and 120° C., preferably 60°–100° C.;

the use of protic and dipolar aprotic solvents, preferably water, $H_2O$/EtOH mixture, dimethylacetamide (DMA), methyl cellosolve and ethyl cellosolve.

The ether bond formation between the compounds of formula (II) and those of formula (III) implies a nucleophilic substitution reaction which involves inversion of configuration when in the compound of general formula (III) a chiral carbon is present.

In view of the results of this invention, we can desume that, considering the same leaving group in the compound of general formula (III), as the protonating ability of the solvent increases (i.e. the capacity of the solvent of donating protons for the formation of hydrogen bonding), the most optically pure product is obtained.

The resulting amides can be used in Smiles rearrangement reactions, under the conditions cited in patent EP 365541 to obtain diagnostic compounds, such as Iopamidol (Examples 1, 3 and 4).

The isolation of the compounds of general formula (I) is carried out according to the methods known in the practice of organic chemistry. Often, through the use of ion exchange resins, or electrodialysis or tangential filtration techniques using filtration membranes, the salts, bases or acids should be removed from the resulting water-soluble compounds.

The following examples are meant for the illustration of the best possible experimental conditions in order to carry out the process of this invention.

EXAMPLE 1

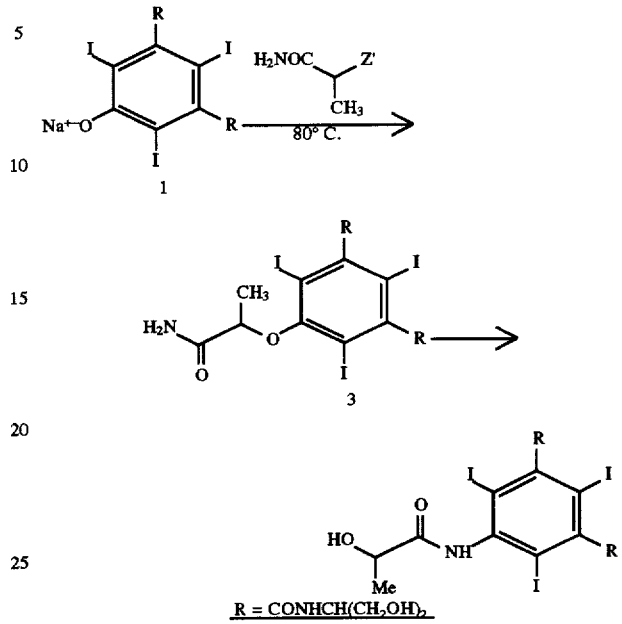

R = $CONHCH(CH_2OH)_2$

| | Z' | Solvent 1 → 3 | Lactate/ fenate (mol/mol) | Recovery yield in 2 steps | Optical purity | Chemical purity |
|---|---|---|---|---|---|---|
| 1 | TsO | DMA | 2 | 40 | 67 | 96 |
| 2 | TsO | Methylcell. | 2 | 40 | 96 | 99 |
| 3 | TsO | $H_2O$/EtOH | 2 | 56 | 98 | 99 |
| 4 | MsO | Methylcell. | 2 | 30 | 84 | 98 |
| 5 | MsO | Ethylcell. | 2 | 42 | 88 | 98 |
| 6 | MsO | $H_2O$/EtOH | 2 | 40 | 94 | 97 |
| 7 | MsO | $H_2O$ | 2 | 56 | 94 | 98 |
| 8 | Cl | Methylcell. | 2 | 33 | 20 | 98 |
| 9 | Cl | Methylcell.* | 2 | 31 | 13 | 95 |
| 10 | Cl | $H_2O$ | 2 | 40 | 88 | 99 |

*with the addition of KI (0.15 mol equiv. with respect to phenoxide) as catalyst

EXAMPLE 2

(S)-5-(2-amino-1-methyl-2-oxoethoxy)-N,N'-bis[2-hydroxy-1-(hydroxymethyl)ethyl]-2,4,6-triiodo-1,3-benzenedicarboxamide

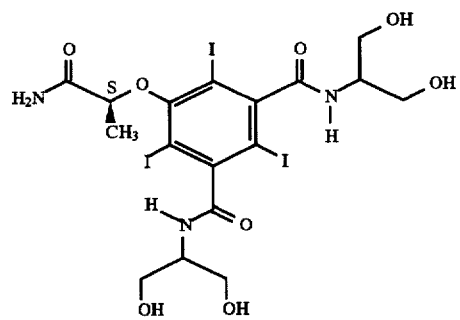

To a solution of 21.8 g of N,N'-bis[2-hydroxy-1-(hydroxymethyl)ethyl]-5-hydroxy-2,4,6-triiodo-1,3-benzenedicarboxamide sodium salt (prepared according to the procedure described in patent EP 185130) (0.03 mol) in 70 mL of methyl cellosolve, heated to 80° C., 14.6 g of R-2-[[(4-methylphenyl)sulfonyl]oxy]propanamide (prepared according to the procedure described in Markert, F. Chem. Ber. 1927, 60, 2456) (0.056 mol) are added and the resulting mixture is kept under stirring in the same conditions for 8 h. After removing methyl cellosolve by evaporation under reduced pressure, the oily residue is treated with CH$_2$Cl$_2$ (2×250 mL). The solid, filtered and dried is dissolved in abs. EtOH (190 mL) and after filtration of sodium p-toluensulfonate, the solution is concentrated to dryness. The treatment is repeated with abs. EtOH (150 mL) and after evaporation the resulting residue is crystallized from abs. EtOH (75 mL). 10.5 g of the desired product (0.0135 mol) are recovered.

Yield: 45% m.p.: 110° C. $[\alpha]_{20}^D$=−22.90° (c 5% CH$_3$OH). TLC: silica gel plate 60F 254 Merck. Eluent: CHCl$_3$:CH$_3$OH:NH$_4$OH 25%=6:3:1. Detector: soluble starch and UV light R$_f$=0.22. $^1$H-NMR, $^{13}$C-NMR, IR and MS spectra are consistent with the structure.

EXAMPLE 3

Preparation of IOPAMIDOL starting from (S)-5-(2-amino-1-methyl-2-oxoethoxy)-N,N'-bis[2-hydroxy-1-(hydroxymethyl)ethyl]-2,4,6-triiodo-1,3-benzenedicarboxamide

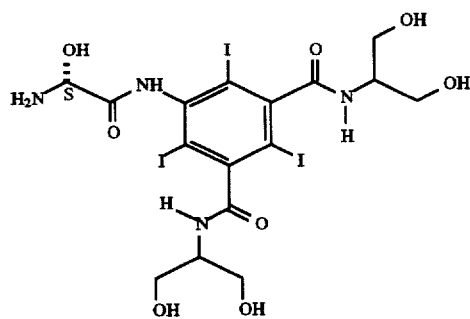

To 10.1 g of (S)-5-(2-amino-1-methyl-2-oxoethoxy)-N,N'-bis[2-hydroxy-1-(hydroxymethyl)ethyl]-2,4,6-triiodo-1,3-benzenedicarboxamide (prepared according to the procedure described in EXAMPLE 2) (0.013 mol) dissolved in 50 mL of MeOH, and maintained under reflux, are swiftly added 56 mL of KOH 1N in MeOH (0.056 mol) then the mixture is refluxed for 2 h. After cooling to room temperature, MeOH is removed by vacuum distillation. The solid residue is diluted in water (100 mL) and percolated on cation exchange resin Amberlite® IR 120 and anion exchange resin Duolite® A 30B eluted with water. After evaporation of the aqueous solution the residue is crystallized from EtOH (35 mL) to give 8.9 g of the desired product (0.0114 mol).

Yield: 88%. Sample purity: 99.8%. $[\alpha]_{436}^{20}$=+137.00° (c=1.25% w/v as Cu(II) complex), optical purity 96% [literature $[\alpha]_{436}^{20}$=+142.28°±0.13°] $^1$H-NMR, $^{13}$C-NMR, IR and MS spectra are consistent with the structure.

EXAMPLE 4

Preparation of IOPAMIDOL starting from N,N'-bis[2-hydroxy-1-(hydroxymethyl)ethyl]-5-hydroxy-2,4,6-triiodo-1,3-benzenedicarboxamide To a solution of 17.20 g of N,N'-bis[2-hydroxy-1-(hydroxymethyl)ethyl]-5-hydroxy-2,4,6-triiodo-1,3-benzenedicarboxamide sodium salt (prepared according to the procedure described in patent EP 185130) (0.0236 mol) in 60 mL of a H$_2$O/EtOH 4/1 mixture, heated to 80° C., 11.5 g of R-2-[[(4-methylphenyl)sulfonyl]oxy]propanamide (prepared according to the procedure described in Markert, F. Chem. Ber. 1927, 60, 2456)(0.056 mol) are added and the resulting mixture is kept under stirring for 8 h. After removal of the solvent by evaporation under reduced pressure, the oily residue is treated with CH$_2$Cl$_2$(2×250 mL). The solid, filtered and dried, is dissolved in abs. EtOH (190 mL) and after filtration of sodium p-toluensulfonate, the solution is concentrated to dryness. To the solution of the residue (70 mL MeOH) refluxing, 81 mL on 1N KOH in MeOH (0.0811) are swiftly added and the heating is kept during 2 h. After cooling to room temperature, MeOH is removed by vacuum distillation. The residual solid is diluted in water (100 mL) and percolated on a cation exchange resin Amberlite® IR 120 and on an anionic exchange resin Duolite® A 30B eluted with water. After evaporation of the aqueous solution the residue is crystallized from EtOH (50 mL) to give 10.2 g of the desired product (0.0131 mol).

Yield: 56% yield in two steps. $[\alpha]_{20}^D$=+138.88° (c=1.25% w/v as Cu$^{(II)}$ complex), optical purity 96% [literature $[\alpha]_{436}^{20}$=+142.28°±0.13°] $^1$H-NMR, $^{13}$C-NMR, IR and MS spectra are consistent with the structure.

We claim:

1. A process for the preparation of compounds of general formula (I)

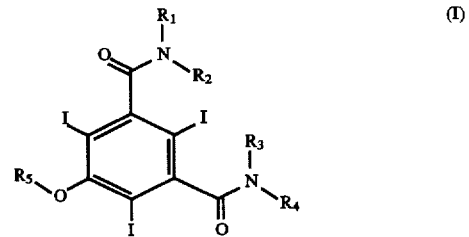

wherein

R1, R2, R3, R4, which can be the same or different, are, independently, H or a linear or branched (C1–C10) alkyl group, optionally substituted by 1–6 hydroxy and/or alkoxy groups, or a polyoxaalkyl group comprising from 1 to 10 oxygen atoms and from 3 to 30 carbon atoms, or R1 and R2 or R3 and R4, taken together, form a (C2–C8) chain optionally interrupted by one or more N, O, S atoms, R5 is the group

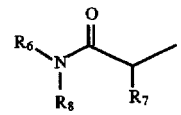

wherein

R$_6$ and R$_8$ are H,

R7 is H or a (C1–C3) alkyl, hydroxyalkyl or alkoxyalkyl group, characterized in that the corresponding derivatives of general formula (II)

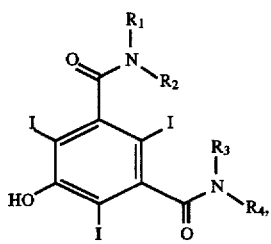

wherein R1, R2, R3 and R4 are as previously defined and the hydroxy group on the benzene ring can be also present as salt of alkali metal or alkaline-earth metal or a (C2–C6) trialkylamine, are reacted with the compounds of general formula (III)

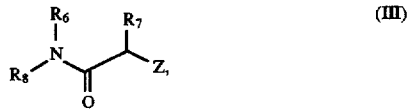

wherein

Z is halogen atom or a reactive residue of a sulfonic acid selected from the group consisting of methanesulfonyloxy, benzenesulfonyloxy and toluene- sulfonyloxy or a —N+(R9)3 cation wherein R9 is a (C1–C6) alkyl group and R6 R7 and R8 are as previously defined;

and the reaction is carried out in a reaction solvent selected from the group consisting of protic solvents and dipolar aprotic solvents.

2. A process according to claim 1, wherein the compound of formula (II) is in the form of sodium salt.

3. A process according to claim 1, wherein the stoichiometric ratio of the compound of formula (III) and the compound of formula (II) is equal to 2.

4. A process according to claim 1, wherein the ether bond formation between the compounds of general formula (II) and the compounds of general formula (III) is carried out at a temperature comprised between room temperature and 120° C.

5. A process according to claim 1, wherein the reaction solvent is selected from the group consisting of: H2O, H2O/EtOH mixture, dimethylacetamide (DMA), methyl cellosolve and ethyl cellosolve.

* * * * *